US008900305B2

(12) United States Patent
Stad et al.

(10) Patent No.: US 8,900,305 B2
(45) Date of Patent: Dec. 2, 2014

(54) INTERVERTEBRAL DEVICE HAVING EXPANDABLE ENDPLATES

(71) Applicants: Shawn Stad, Lakeville, MA (US); Christopher Ramsay, West Wareham, MA (US)

(72) Inventors: Shawn Stad, Lakeville, MA (US); Christopher Ramsay, West Wareham, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 14/028,934

(22) Filed: Sep. 17, 2013

(65) Prior Publication Data

US 2014/0018921 A1 Jan. 16, 2014

Related U.S. Application Data

(63) Continuation of application No. 13/281,833, filed on Oct. 26, 2011, now Pat. No. 8,574,297, which is a continuation of application No. 11/694,524, filed on Mar. 30, 2007, now Pat. No. 8,137,401.

(51) Int. Cl.
*A61F 2/44* (2006.01)
*A61F 2/30* (2006.01)

(52) U.S. Cl.
CPC ......... *A61F 2/442* (2013.01); *A61F 2220/0091* (2013.01); *A61F 2002/30476* (2013.01); *A61F 2/4425* (2013.01); *A61F 2002/30604* (2013.01); *A61F 2/4455* (2013.01); *A61F 2002/30151* (2013.01); *A61F 2230/0017* (2013.01); *A61F 2220/0033* (2013.01); *A61F 2002/30383* (2013.01); *A61F 2220/0025* (2013.01); *A61F 2002/30579* (2013.01); *A61F 2002/30471* (2013.01); *A61F 2/441* (2013.01); *A61F 2002/3037* (2013.01)
USPC ........................................................ 623/17.15

(58) Field of Classification Search
USPC ........................................................ 623/17.15
See application file for complete search history.

(56) References Cited

U.S. PATENT DOCUMENTS

| 5,928,284 | A | 7/1999 | Mehdizadeh |
| 6,102,950 | A | 8/2000 | Vaccaro |
| 6,723,126 | B1 | 4/2004 | Berry |
| 7,101,375 | B2 | 9/2006 | Zucherman |
| 8,137,401 | B2 | 3/2012 | Stad |
| 8,574,297 | B2 | 11/2013 | Stad |

(Continued)

FOREIGN PATENT DOCUMENTS

WO 2006058281 10/2006

*Primary Examiner* — Bruce E Snow
*Assistant Examiner* — Brian Dukert
(74) *Attorney, Agent, or Firm* — Raymond N. Scott, Jr.

(57) ABSTRACT

An intervertebral implant having an endplate that can be slidably expanded following its placement in the intervertebral space. The endplate comprises a pair of planks that are slidably received within respective recesses of a base portion of the endplate. During insertion of the implant into the intervertebral space, the planks are set in a contracted position within respective recesses of a base portion of the endplate. This provides the implant with a relatively small profile that is suitable for MIS procedures. Once the implant has been inserted, the planks are slid outward from the recesses to an expanded position that increases the footprint of the implant endplate. This expansion increases the stability of the implant.

16 Claims, 8 Drawing Sheets

(56) References Cited

U.S. PATENT DOCUMENTS

| | | |
|---|---|---|
| 2004/0030387 A1 | 2/2004 | Landry |
| 2004/0087947 A1 | 5/2004 | Lim |
| 2004/0088054 A1* | 5/2004 | Berry .......................... 623/17.11 |
| 2005/0060037 A1 | 3/2005 | Michelson |
| 2005/0071007 A1 | 3/2005 | Malek |
| 2005/0197702 A1 | 9/2005 | Coppes |
| 2005/0209698 A1 | 9/2005 | Gordon |
| 2005/0256576 A1 | 11/2005 | Moskowitz |
| 2006/0224241 A1 | 10/2006 | Butler |
| 2007/0055378 A1 | 3/2007 | Ankney |

* cited by examiner

INTERVERTEBRAL DEVICE HAVING EXPANDABLE ENDPLATES

CONTINUITY DATA

This application claims priority from co-pending U.S. Ser. No. 13/281,833, filed Oct. 26, 2011, to Stad, entitled "Intervertebral Device Having Expandable Endplates", the specification of which is incorporated by reference in its entirety, which claims priority from U.S. Ser. No. 11/694,524, filed Mar. 30, 2007, to Stad, entitled "Intervertebral Device Having Expandable Endplates", (Now U.S. Pat. No. 8,137,401), the specification of which is incorporated by reference in its entirety.

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

Since first generation motion discs were inserted anteriorly, the size of the disc's endplate did not hinder the insertion technique and so was essentially equal to the size of the vertebral endplates opposing the motion disc. However, later generation motion discs seek to insert the motion disc from the posterior or posterolateral directions. These methods of insertion seek to minimize the size of the portal through which the motion disc is inserted. However, such a minimized profile may unacceptable reduce the size of the prosthetic endplate.

Thus, it is an object of the present invention to provide a motion disc that can be inserted from the posterior or posterolateral directions and that has a relatively large endplate footprint.

US2005/0060037 (Michelson) describes an interbody spinal fusion implant having an expandable height and interlocking side walls to maintain the increased height of the implant. More particularly, it describes a threaded fusion cage having adjustable lordosis.

US2005/0071007 (Malek) describes intervertebral disc prostheses that have adjustable disc heights, that are readily converted into fusion prostheses and that provide a range of motions that effectively mimic the natural range of motions of a spinal disc.

US2005/0256576 (Moskowitz) describes an total artificial expansible disc having at least two pairs of substantially parallel shells, which move in multiple directions defined by at least two axes, is disclosed. Several methods for implanting the total artificial expansile disc are also disclosed. The total artificial expansile disc occupies a space defined by a pair of vertebral endplates. An expansion device moves the pairs of shells in multiple directions. A core is disposed between the pairs of shells, and the core permits the vertebral endplates to move relative to one another.

US2005/0209698 (Gordon) describes an artificial functional spinal unit including an expandable intervertral implant that can be inserted via a posterior surgical approach and used with one or more facet replacement devices to provide an anatomically correct range of motion. Lordotic and non-lordotic expandable, articulating implants and cages and methods of insertion are also described. Gordon further describes an advancing element that can increase height.

US2005/0197702 (Coppes) describes a fixed size endplate having an inflatable middle. Coppes relates to an artificial intervertebral disc for placement between adjacent vertebrae. The artificial intervertebral disc is preferably designed to restore disc height and lordosis, allow for a natural range of motion, absorb shock and provide resistance to motion and axial compression. Furthermore, the intervertebral disc may be used in the cervical, the thoracic, or the lumber regions of the spine. The artificial intervertebral disc may include either singularly or in combination: an interior at least partially filled with a fluid; a valve for injecting fluid into the interior of the disk; a central region having a stiffness that is preferably greater than the stiffness of the outer regions thus enabling the disc to pivot about the central region. The central pivot may be formed by a center opening, a central chamber, an inner core or a central cable.

WO2006058281 ("Glenn") discloses a spinal implant to be inserted between two vertebra to support and stabilize adjacent vertebra and allow for physiological motion. The invention includes an implantable device to support the vertebrae, and a minimally invasive method for inserting and deploying the device within the intervertebral space

SUMMARY OF THE INVENTION

The present invention relates to an intervertebral implant having an endplate that can be expanded following its placement in the intervertebral space.

In a first embodiment, the endplate comprises a pair of planks that are slidably received within respective recesses of a base portion of the endplate. During insertion of the implant into the intervertebral space, the planks are set in a contracted position within respective recesses of a base portion of the endplate. This provides the implant with a relatively small profile that is suitable for MIS procedures. Once the implant has been inserted, the planks are slid outward from the recesses to an expanded position that increases the footprint of the implant endplate. This expansion increases the stability of the implant.

Therefore, in accordance with the present invention, there is provided an intervertebral implant device having an expandable endplate, the endplate comprising:
  a) a first base portion having an outer surface adapted for bearing against a natural endplate, an inner surface, first and second side surfaces extending between the outer and inner surfaces, a first cutout opening onto the outer surface and the first side surface and forming a first recessed surface, and
  b) a first plank slidingly receivable within the first cutout and adapted to translate across the first recessed surface.

DETAILED DESCRIPTION OF THE INVENTION

Figure 1:
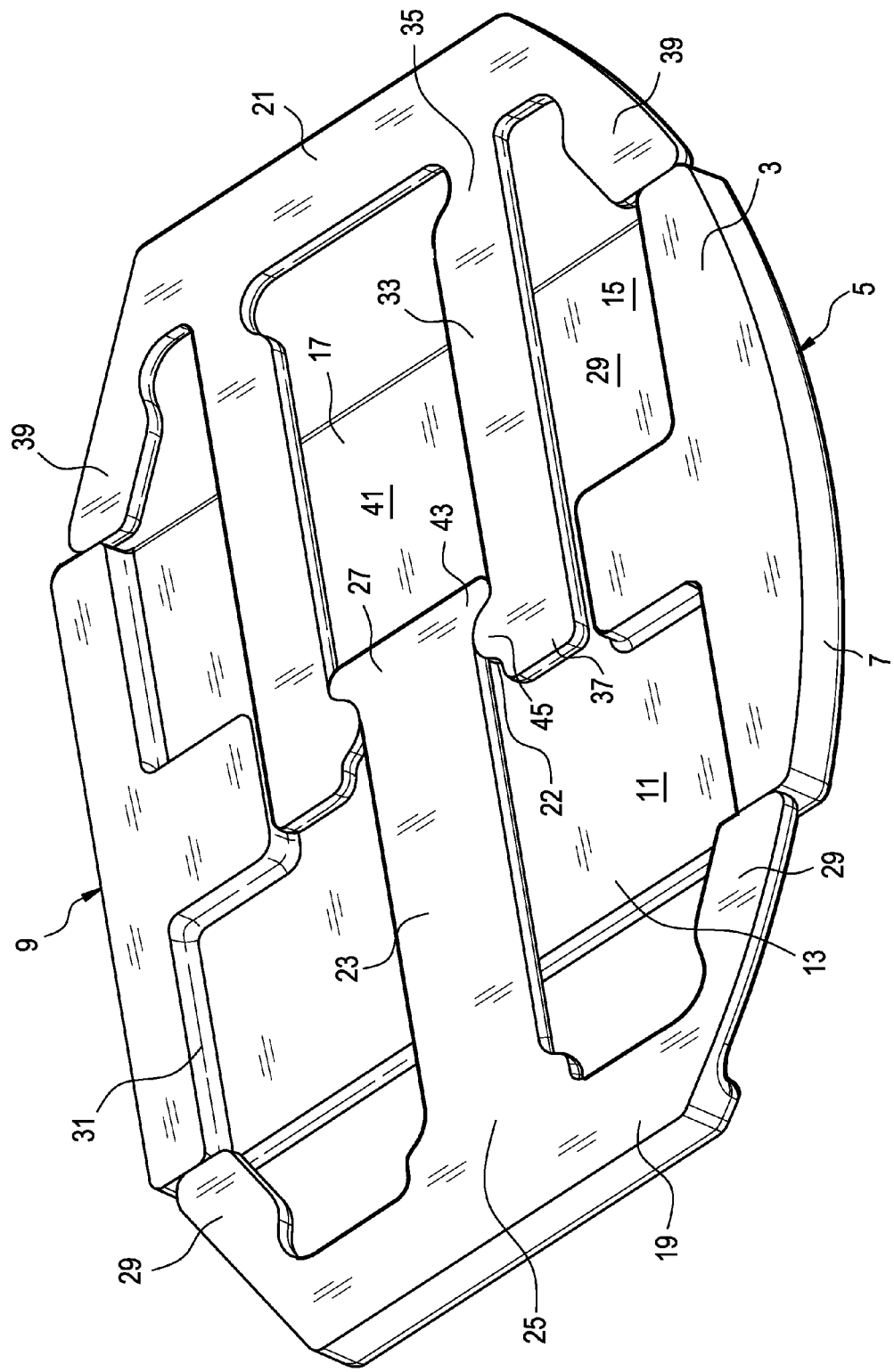
FIG. 1 is a perspective view of an endplate of the present invention having its second base portion removed to fully expose the planks therein.

Now referring to FIG. 1, there is provided an intervertebral prosthetic device having an expandable endplate, comprising:
- a) a first base portion 1 having an outer surface 3 adapted for bearing against a natural endplate, an inner surface 5, first 7 and second 9 side surfaces extending between the outer and inner surfaces, a first cutout 11 opening onto the outer surface and the first side surface and forming a first recessed surface 13, and a second cutout 15 opening onto the outer surface and the second side surface and forming a second recessed surface 17,
- b) a first plank 19 slidingly receivable within the first cutout and adapted to translate across the first recessed surface, and
- c) a second plank 21 slidingly receivable within the second cutout and adapted to translate across the second recessed surface.

In this embodiment, the first and second cutouts are joined by a third recessed surface 22 in the outer surface of the first base portion.

The first plank of this embodiment has a substantially T shape having a first shaft portion 23 having an first outer end portion 25, a first inner end portion 27 and a first pair of flexible arms 29 extending from the outer end portion During insertion, the first pair of flexible arms is received in the first cutout in a contracted position (not shown) in order to minimize the profile of the endplate. The contraction of the arms is caused by the flexible arms bearing against an inner rim 31 of the cutout. After insertion, the plank is slid outwards from the cutout (as shown in FIG. 1), and the first pair of flexible arms becomes free of the bias of the inner rim of the cutout, and thereby expands. Likewise, the second plank of this embodiment also has a substantially T shape having a second shaft portion 33 having a second outer end portion 35, a second inner end portion 37 and a second pair of flexible arms 39 extending from the outer end portion. It behaves substantially similarly to the first plank during insertion and expansion, sliding from a contracted position to an expanded position.

The two planks are designed to interweave with one another in both the contracted and expanded positions. The endplate is designed so that the first outer end portion of the first plank is slidably received in a recess 41 in the second inner end portion of the second plank. In the contracted state, the first outer end portion of the first plank is nearly fully received in a recess in the second inner end portion of the second plank. After expansion, a first flange 43 extending from the first outer end portion of the first plank bears against a second flange 45 extending from the second outer end portion of the second plank, thereby preventing further outward movement of the planks so as to partially stabilize the expanded position construct.

Also in the expanded position, the end portions of the freed flexible arms may now bear against the first side surface of the base portion so as to prevent retraction of the arms back into the cutouts and to stabilize the expanded position construct.

Figure 2:
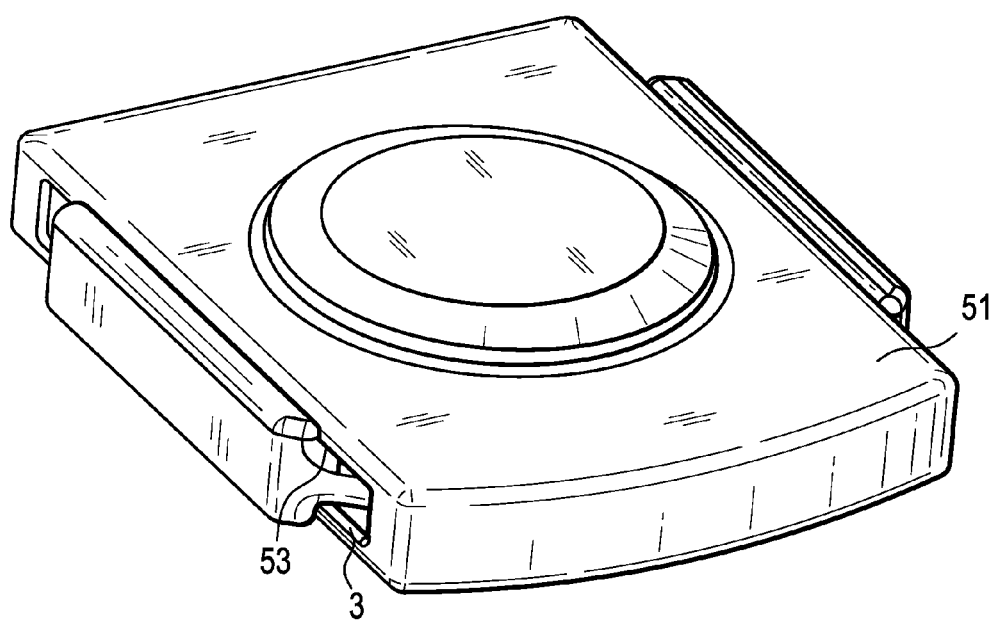
FIG. 2 is a perspective view of an endplate of a motion disc of the present invention, wherein the planks are in a contracted position.

Now referring to FIG. 2, the endplate of FIG. 1 may further comprise:
- c) a second base portion 51 connected with the first base portion and having an inner surface 53 opposing the outer surface 3 of the first base portion to enclose the first plank within the first cutout and the second plank within the second cutout. The purpose of the second base portion is to prevent the planks from moving out of the cutouts, thereby partially stabilizing the expanded position construct.

The coupling of the first and second base portions produces a sleeve into which the planks are slidably received. Therefore, in accordance with the present invention (and now referring to FIG. 3), there is provided an intervertebral prosthetic device having an expandable endplate, the endplate comprising:
- a) a sleeve 61 having an outer surface 63 adapted for bearing against a natural endplate, an inner surface 65, first 67 and second side 69 surfaces extending between the outer and inner surfaces, a first recess 71 extending into the sleeve from the first side surface, and a second recess extending into the sleeve from the first side surface,
- b) a first plank 73 slidably received in the first recess of the sleeve, and
- c) a second plank 75 slidably received in the second recess of the sleeve.

In most embodiments, the inner surface of the endplate has a functional feature thereon. Now referring to FIG. 3, if the implant is an articulating motion disc, then the functional feature is an articulation surface 77. If the implant is a cushion-type motion disc, then the functional feature can be an expandable bag that is attached to each of the inner surfaces of the opposed endplates and then filled with a compliant material after insertion.

Figure 3:
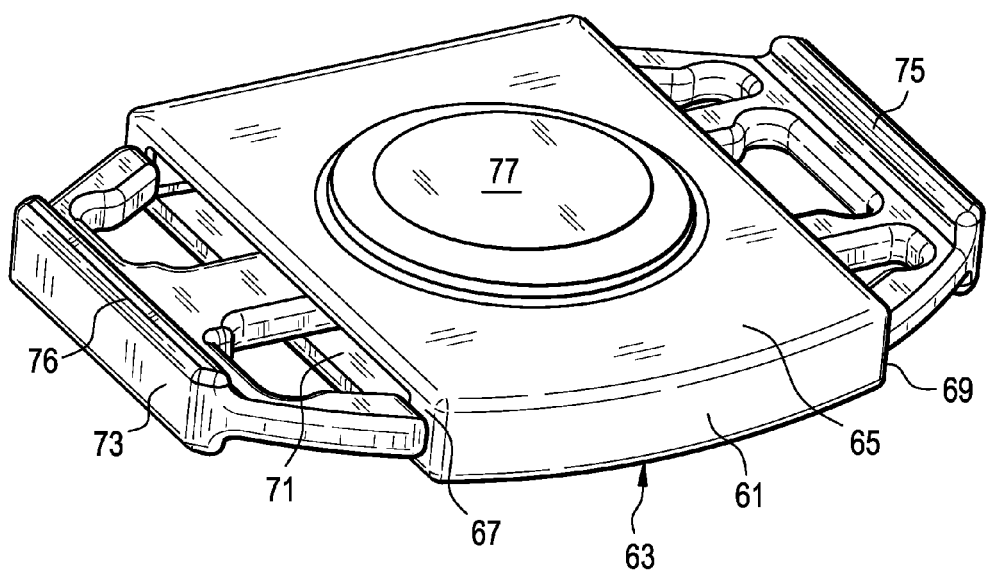
FIG. 3 is a perspective view of an endplate of a motion disc of the present invention, wherein the planks are in an expanded position.

Now referring to FIG. 3, there is provided is a perspective view of an endplate of FIG. 2, wherein the planks are in an expanded position. Extending from the outer end portion of the T shaped plank is handle 76. After insertion, these handles are pulled outwardly to expand the endplate.

Figure 4A:
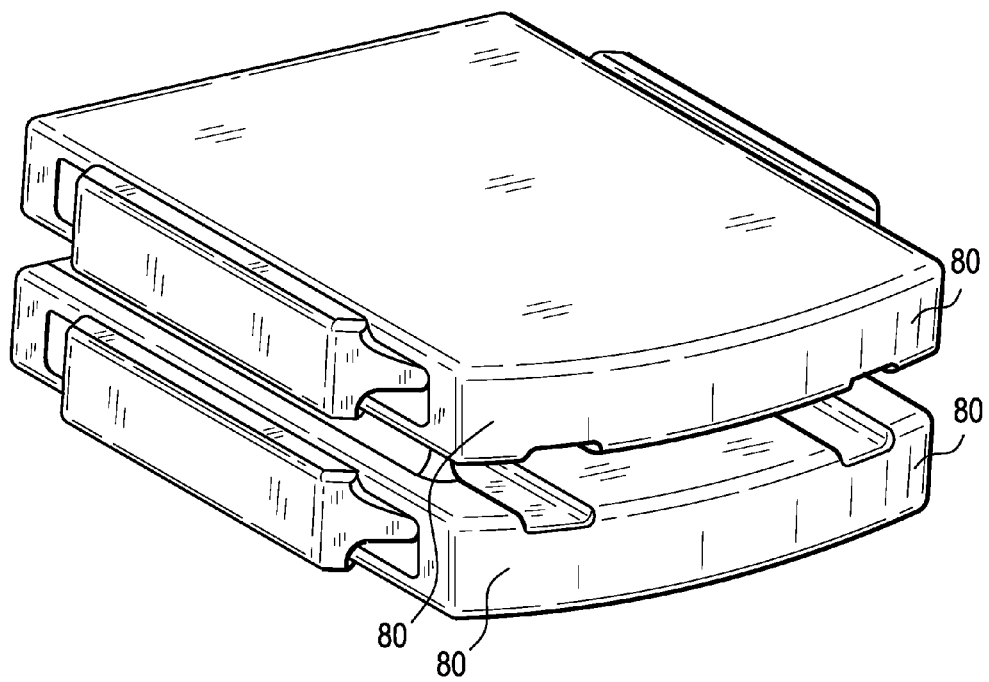
FIG. 4a is a perspective view of a pair of opposed endplates of the present invention, wherein the planks are in a contracted position.
Figure 4B:
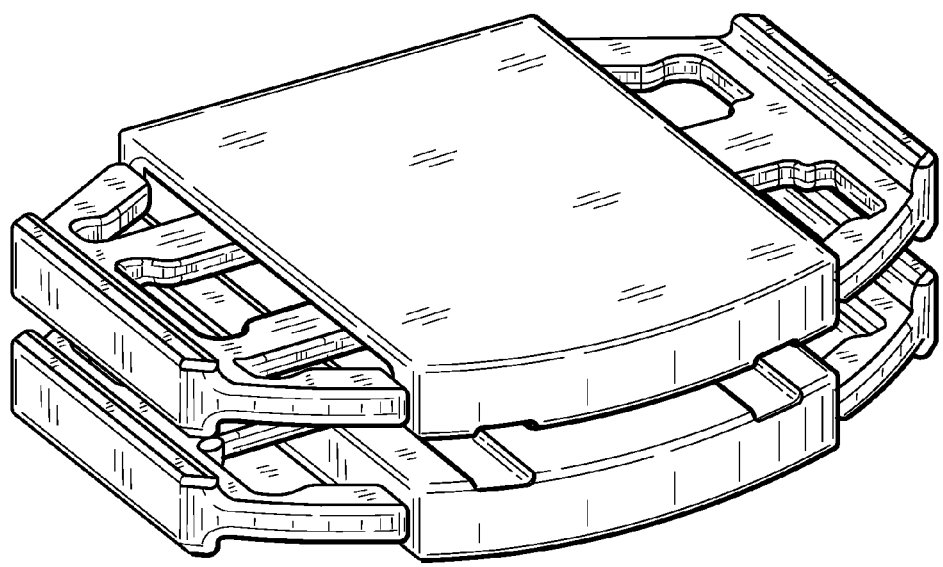
FIG. 4b is a perspective view of the pair of opposed endplates of FIG. 4a, wherein the planks are in an expanded position.
Figure 4C:
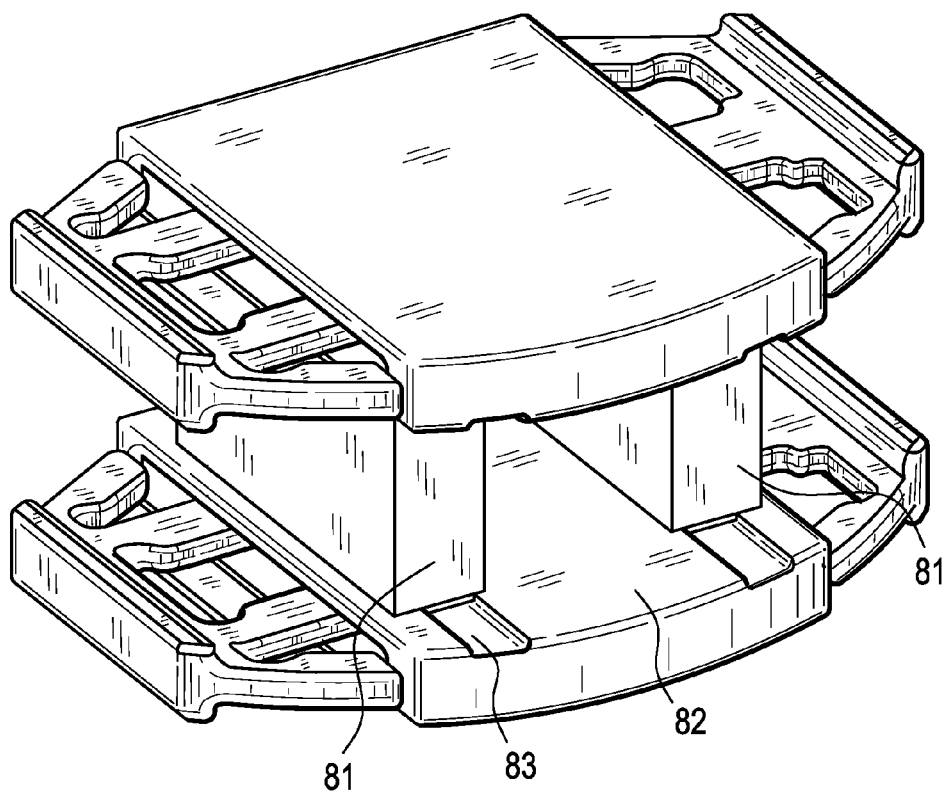
FIG. 4c is a perspective view of the pair of opposed endplates of FIG. 4b having intervertebral struts placed therebetween.

Now referring to FIG. 4a, if the implant is to be a fusion cage, then it is desirable to use two endplates 80 having sleeves to enclose planks, shown here in their contracted position. FIG. 4b shows the endplates provided in an opposed relationship with their planks in an expanded position. FIG. 4c is a perspective view of the pair of opposed endplates of FIG. 4b having intervertebral struts 81 placed therebetween. In FIGS. 4a-4c, the functional feature upon the inner surface 82 of the endplate is adapted to connect to a first load-bearing strut. In these fusion cage embodiments, the embodiment may further include a second functional feature adapted to connect to a second load-bearing strut. In FIGS. 4a-4c, the functional feature is a recessed groove 83.

In fusion-type embodiments, it may be desirable to provide endplates having throughholes extending between the inner and outer surfaces of the endplates so as to accommodate fusion. This may be accomplished by providing holes through the first and second base portions of each endplate. These throughholes are adapted to provide bone growth therethrough in order to facilitate the fusion of the disc space.

In some fusion-type embodiments (not shown), the struts are provided with an angle, of typically between about 5 and about 15 degrees. These angled struts may be used to provide the endplate with a lordotic orientation.

In some embodiments of the present invention, the endplate is made expandable by providing pivoting planks within a sleeve.

Figure 5:
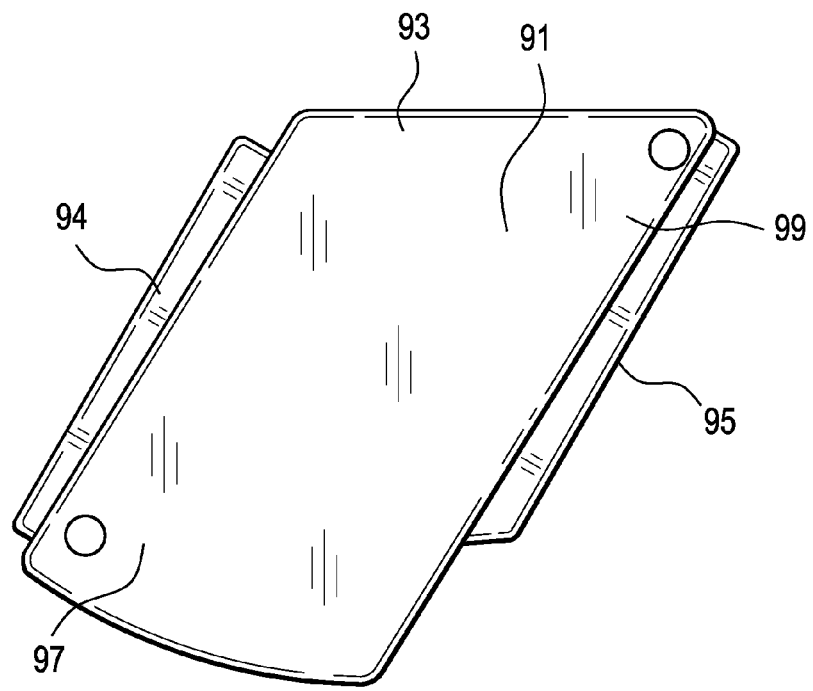
FIG. 5 discloses a parallelogram-type endplate having pivoting planks in a contracted state.
Figure 6:
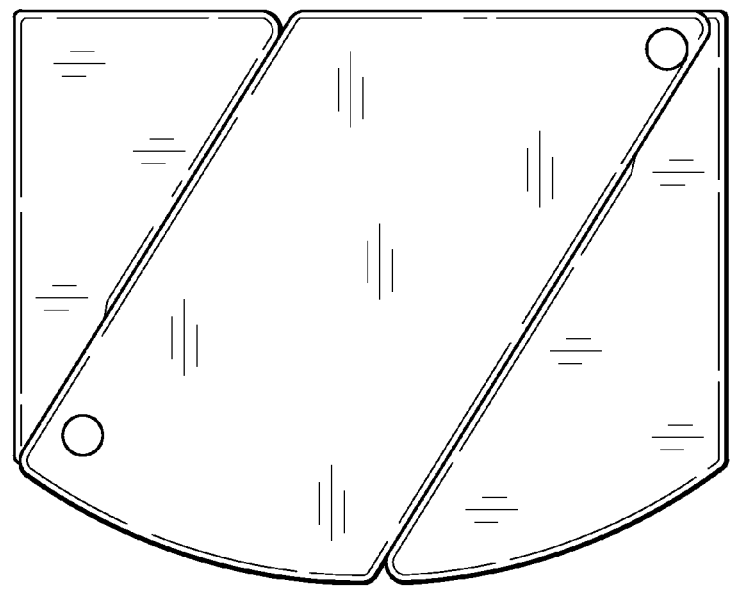
FIG. 6 discloses a parallelogram-type endplate having pivoting planks in an expanded state.

Now referring to FIGS. 5 and 6, there is provided an intervertebral prosthetic device having an expandable endplate, the endplate comprising:
- a) a sleeve 91 having an outer surface 93 adapted for bearing against a natural endplate, an inner surface, first and second side surfaces extending between the outer and inner surfaces, a first recess extending into the sleeve from the first side surface, and a second recess extending into the sleeve from the first side surface,
- b) a first plank 94 slidably received in the first recess of the sleeve and pivotally connected to the sleeve, and
- c) a second plank 95 slidably received in the second recess of the sleeve and pivotally connected to the sleeve.

In this particular embodiment, the sleeve itself has a substantially parallelogram shape comprising a first acute corner 97 and a second opposite acute corner 99. The first plank is pivotally connected to the sleeve in the first acute corner of the sleeve, and the second plank is pivotally connected to the sleeve in a second opposite acute corner of the sleeve.

In use, the endplates are inserted into the disc space in a contracted position. Once the endplates are in the disc space, the planks are swung out of their respective recesses to their expanded positions. In this particular embodiment, the expanded configuration forms a D-shaped footprint, thereby mimicking the footprint of the natural vertebral endplate.

Figure 7:
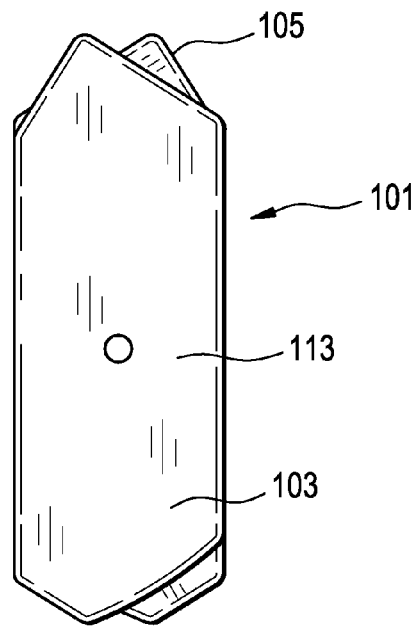
FIG. 7 discloses a fan-type endplate having pivoting planks in a contracted state.
Figure 8:
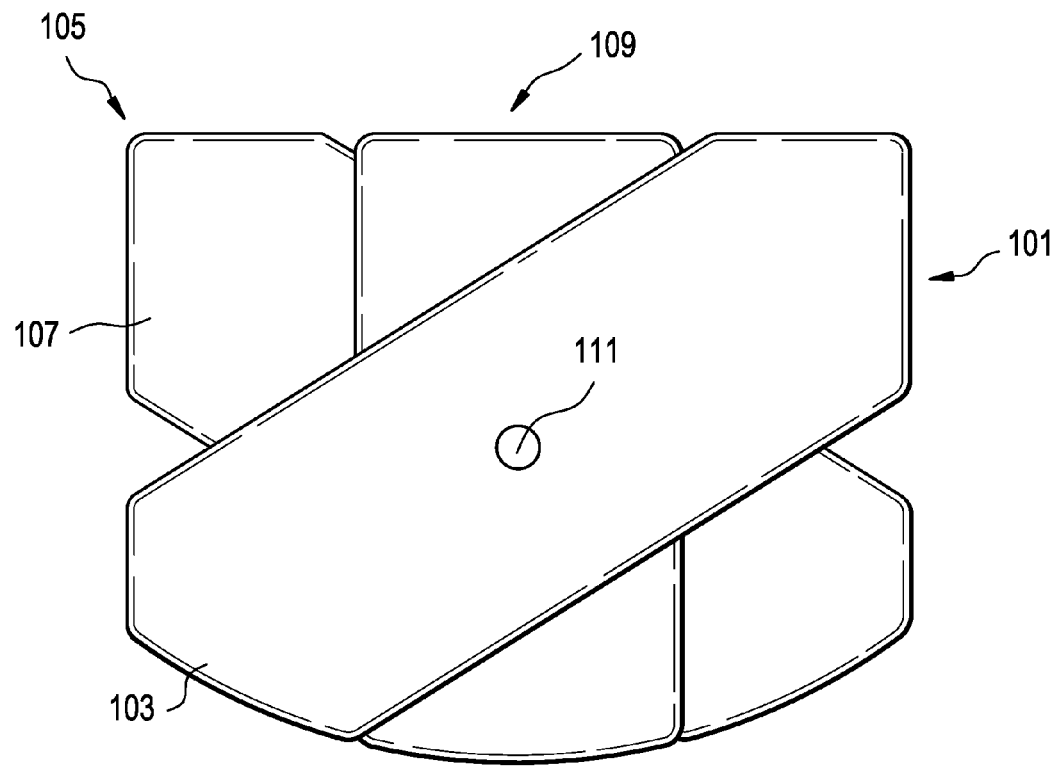
FIG. 8 discloses a fan-type endplate having pivoting planks in an expanded state.

Now referring to FIGS. 7 and 8, there is provided an intervertebral prosthetic device having an expandable endplate, the endplate comprising:
- a) a first outer plank 101 having an outer surface 103 adapted for bearing against a natural endplate, and an inner surface, and a first throughhole extending between the outer surface and the inner surface thereof,
- b) a second outer plank 105 having an outer surface adapted for bearing against a natural endplate, and an inner surface 107, and a second throughhole extending between the outer surface and the inner surface thereof,
- c) an inner plank 109 disposed between the inner surfaces of the outer planks and having a third throughhole extending therethrough, and
- d) a pivot pin 111 extending through each of the throughholes to pivotally connect the planks.

As shown in FIGS. 7 and 8, the pivot pin extends substantially through a midportion 113 of each plank.

In use, the endplate is inserted into the disc space in a contracted, aligned position. Once the endplate is in the disc space, the planks are rotated about the pivot pin from their respective aligned positions to take their expanded positions. In this particular embodiment, the expanded configuration forms a D-shaped footprint, thereby mimicking the footprint of the natural vertebral endplate.

In some embodiments, at least some of the plank surfaces are recessed to provide nesting with an adjacent plank. This nesting feature not only can allow the individual surfaces of the adjacent planks to combine into a single planar surface, it also locks the planks into their desired orientation.

Preferably, the outer surface of an endplate of the present invention can be either flat, curved or domed to match the natural vertebral endplate. Alternatively, the geometry of the inferior surface can be designed so that it will match the shape of the patient's vertebral endplate after the vertebral endplate has been modified by an endplate-shaping instrument. In addition, the outer surface of this endplate can further comprise features to promote and secure initial fixation and bony ingrowth including, but not limited to, spikes, keels, teeth, projections (such as dovetails), recesses (such as grooves), throughholes and porous coatings.

We claim:

1. A method comprising the steps of:
   - a) inserting into a disc space an intervertebral implant device having an expandable endplate, the endplate comprising:
     - a) a first base portion having an outer surface adapted for bearing against a natural endplate, an inner surface, first and second side surfaces extending between the outer and inner surfaces, a first cutout opening onto the outer surface and the first side surface and forming a first recessed surface, and
     - b) a first plank slidingly receivable within the first cutout and adapted to translate across the first recessed surface, wherein the first plank has a first shaft portion having a first outer end portion, a first inner end portion and a first pair of flexible arms extending from the outer end portion, and
   wherein the plank is set in a contracted position within the first recessed surface, and
   - b) sliding the plank outward from the recessed surface to an expanded position.

2. The method of claim 1 wherein the base portion further comprises a second cutout opening onto the outer surface and the second side surface and forming a second recessed surface, and wherein the endplate further comprises:
   - c) a second plank slidingly receivable within the second cutout and adapted to translate across the second recessed surface.

3. The method of claim 2 wherein the first and second cutouts are joined by a third recessed surface in the inner surface of the first base portion.

4. The method of claim 3 wherein the first plank has a substantially T shape having a first shaft portion having a first outer end portion, a first inner end portion and a first pair of arms extending from the outer end portion.

5. The method of claim 1 wherein the expanded position increases a footprint of the implant device.

6. The method of claim 5 wherein the first pair of flexible arms are receivable in the first cutout in a contracted position.

7. The method of claim 5 wherein the first pair of flexible arms bear against the first side surface in an expanded position.

8. The method of claim 4 wherein the second plank has a substantially T shape having a second shaft portion having a second outer end portion, a second inner end portion and a second pair of arms extending from the outer end portion.

9. The method of claim 8 wherein the second pair of arms are flexible.

10. The method of claim 9 wherein the second pair of flexible arms are receivable in the second cutout in a contracted position.

11. The method of claim 9 wherein the second pair of flexible arms bear against the first side surface in an expanded position.

12. The method of claim 8 wherein the first outer end portion of the first plank is received in a recess in the second inner end portion of the second plank.

13. The method of claim 1 further comprising:
c) a second base portion connected with the first based portion and having an inner surface opposing the inner surface of the first base portion to enclose the first plank within the first cutout.

14. The method of claim 13 wherein the second base portion further has an outer surface having an articulation surface thereon.

15. The method of claim 13 wherein the second base portion further has an outer surface having a first recess adapted for connection to a first load-bearing strut.

16. The method of claim 15 wherein the load-bearing strut has an angle.

* * * * *